(12) United States Patent
Wendland et al.

(10) Patent No.: US 11,439,770 B2
(45) Date of Patent: Sep. 13, 2022

(54) INJECTION DEVICE

(71) Applicant: SANOFI-AVENTIS DEUTSCHLAND GMBH, Frankfurt am Main (DE)

(72) Inventors: Stefan Wendland, Frankfurt am Main (DE); Michael Harms, Frankfurt am Main (DE); Uwe Dasbach, Frankfurt am Main (DE); Jan Torben Eickriede, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 169 days.

(21) Appl. No.: 15/778,120

(22) PCT Filed: Nov. 21, 2016

(86) PCT No.: PCT/EP2016/078247
§ 371 (c)(1),
(2) Date: May 22, 2018

(87) PCT Pub. No.: WO2017/089259
PCT Pub. Date: Jun. 1, 2017

(65) Prior Publication Data
US 2019/0001070 A1    Jan. 3, 2019

(30) Foreign Application Priority Data
Nov. 27, 2015  (EP) .................... 15196675

(51) Int. Cl.
*A61M 5/32*  (2006.01)
*A61M 5/24*  (2006.01)
*A61M 5/20*  (2006.01)

(52) U.S. Cl.
CPC ........ *A61M 5/3204* (2013.01); *A61M 5/3202* (2013.01); *A61M 5/326* (2013.01);
(Continued)

(58) Field of Classification Search
CPC .............. A61M 5/3204; A61M 5/3271; A61M 5/3272; A61M 5/3243; A61M 5/3245; A61M 2005/3267
See application file for complete search history.

(56) References Cited

U.S. PATENT DOCUMENTS

| 4,976,701 A | 12/1990 | Ejlersen et al. |
| 6,210,369 B1 | 4/2001 | Wilmot et al. |

(Continued)

FOREIGN PATENT DOCUMENTS

| CN | 101166551 | 4/2008 |
| CN | 101939038 | 1/2011 |

(Continued)

OTHER PUBLICATIONS

International Search Report and Written Opinion in International Application No. PCT/EP2016/078247, dated Mar. 7, 2017, 14 pages.

(Continued)

*Primary Examiner* — Nathan R Price
*Assistant Examiner* — Courtney B Fredrickson
(74) *Attorney, Agent, or Firm* — Fish & Richardson P.C.

(57) ABSTRACT

The present disclosure relates to an injection device. The injection device comprises a body for holding a syringe having a needle extending from one end thereof and a cap that is removably attached to the body. The cap has a needle shield to cover said needle. The injection device further comprises a biasing member and a lock. The biasing member is configured to urge at least a part of the cap away from the body. The lock is moveable between a locked state, wherein the lock holds the cap and body together, and an unlocked state, wherein the cap and body are able to move apart.

20 Claims, 13 Drawing Sheets

(52) U.S. Cl.
CPC ............... *A61M 5/20* (2013.01); *A61M 5/24* (2013.01); *A61M 2005/3267* (2013.01)

(56) References Cited

U.S. PATENT DOCUMENTS

| | | | |
|---|---|---|---|
| 6,551,286 B1 | 4/2003 | Claessens | |
| 9,808,582 B2* | 11/2017 | Kramer | A61M 5/2066 |
| 2003/0125677 A1* | 7/2003 | Swenson | A61B 17/205 |
| | | | 604/263 |
| 2004/0144668 A1 | 7/2004 | Marshall et al. | |
| 2004/0236284 A1* | 11/2004 | Hoste | A61M 5/326 |
| | | | 604/198 |
| 2005/0165353 A1 | 7/2005 | Pessin | |
| 2007/0129591 A1* | 6/2007 | Yanke | G21F 5/018 |
| | | | 588/16 |
| 2009/0270672 A1 | 10/2009 | Fago | |
| 2011/0046561 A1 | 2/2011 | Pickhard | |
| 2012/0302989 A1 | 11/2012 | Kramer et al. | |
| 2013/0274671 A1* | 10/2013 | Jennings | A61M 5/20 |
| | | | 604/154 |
| 2014/0025006 A1* | 1/2014 | Takemoto | A61M 5/3245 |
| | | | 604/110 |
| 2014/0221916 A1 | 8/2014 | Kramer et al. | |
| 2014/0371684 A1 | 12/2014 | Holmqvist | |
| 2015/0051553 A1* | 2/2015 | Bjork | A61M 5/3204 |
| | | | 604/198 |
| 2018/0177955 A1* | 6/2018 | Aneas | A61M 5/178 |

FOREIGN PATENT DOCUMENTS

| | | |
|---|---|---|
| CN | 104349807 | 2/2015 |
| EP | 1099450 | 5/2001 |
| EP | 1385564 | 2/2004 |
| EP | 1690562 | 8/2006 |
| EP | 2926861 | 10/2015 |
| EP | 3106190 | 12/2016 |
| JP | 2003-199751 | 7/2003 |
| JP | 2004-528939 | 9/2004 |
| JP | 2004-531316 | 10/2004 |
| JP | 2005-520602 | 7/2005 |
| WO | WO 02/087670 | 11/2002 |
| WO | WO 02/100467 | 12/2002 |
| WO | WO 2006/017732 | 2/2006 |
| WO | WO 2012/137803 | 10/2012 |
| WO | WO 2013/178599 | 12/2013 |
| WO | WO 2013/135566 | 1/2014 |
| WO | WO 2015/001819 | 1/2015 |
| WO | WO 2015/090320 | 6/2015 |

OTHER PUBLICATIONS

International Preliminary Report on Patentability in International Application No. PCT/EP2016/078247, dated May 29, 2018, 10 pages.

* cited by examiner

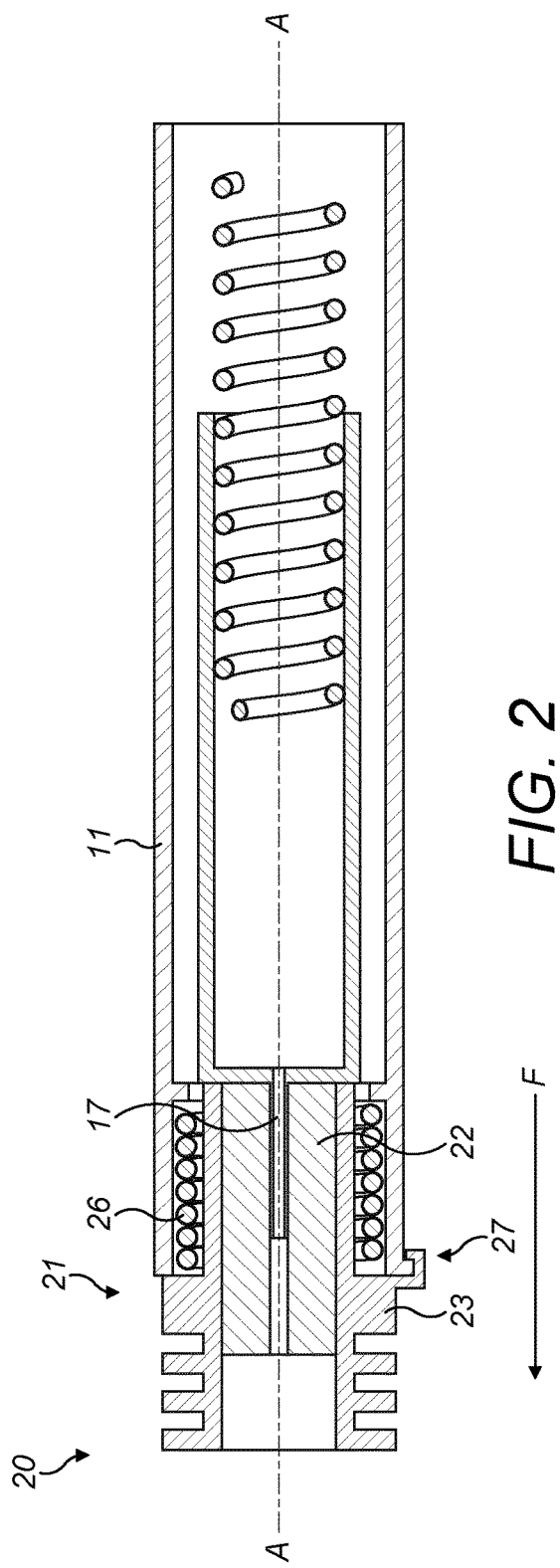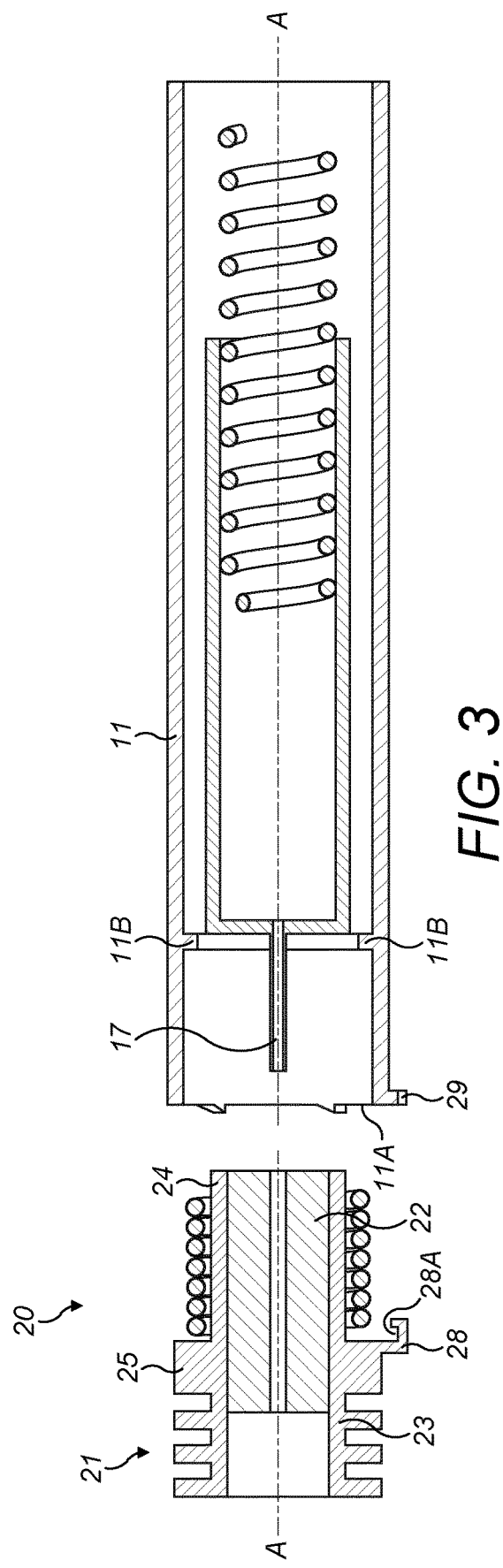

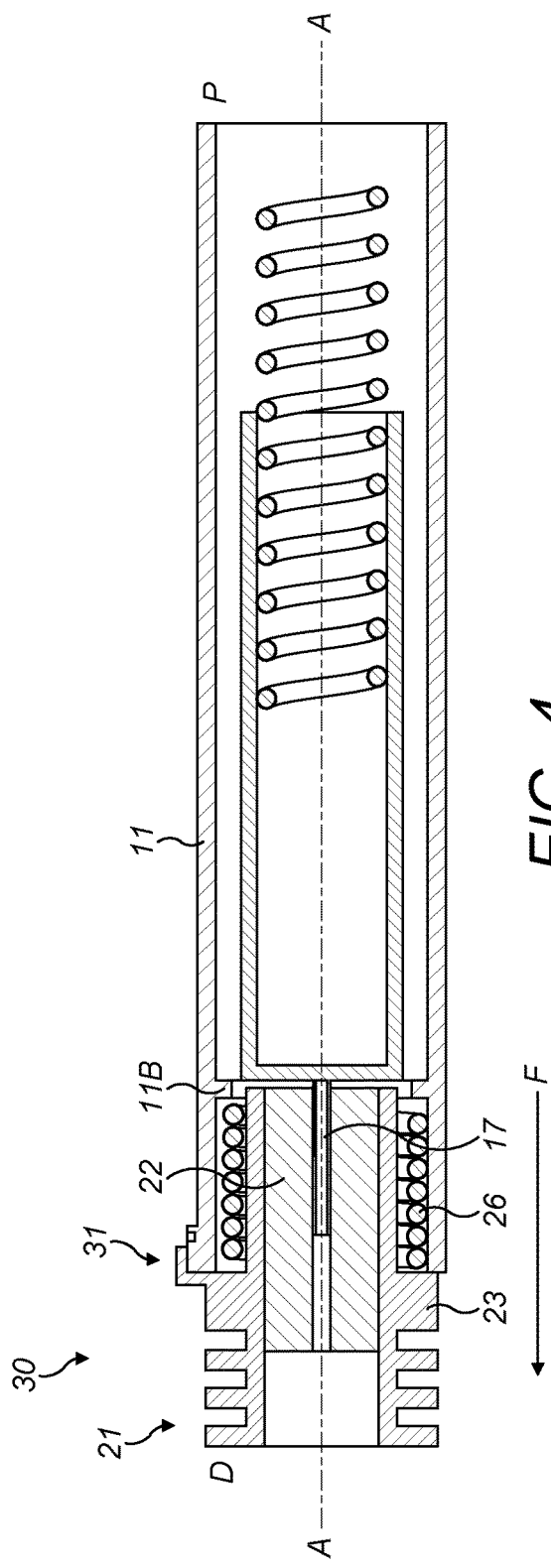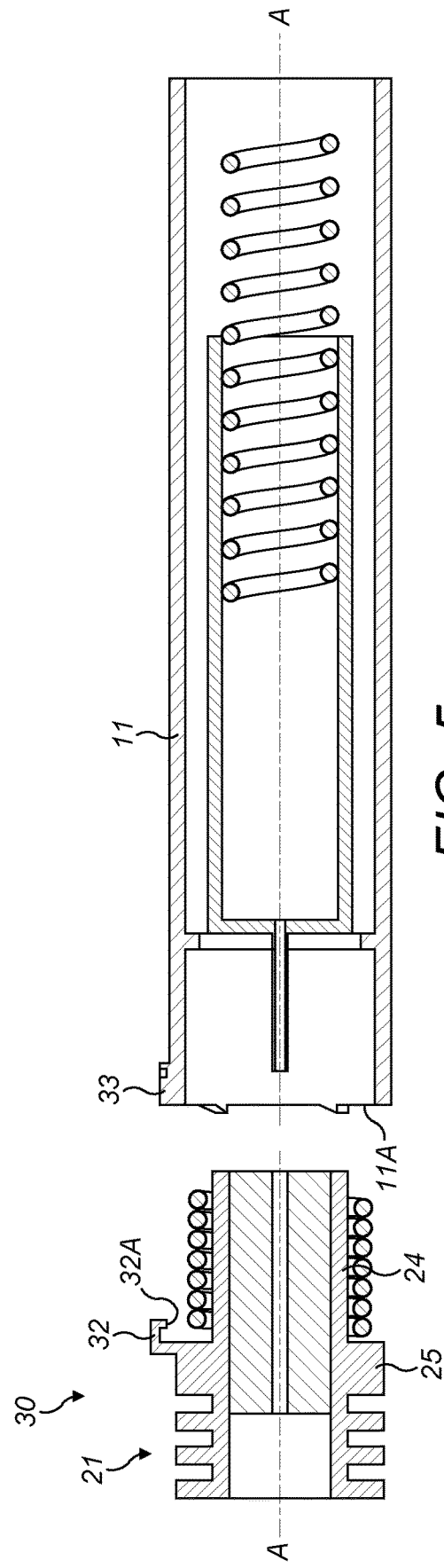

INJECTION DEVICE

CROSS REFERENCE TO RELATED APPLICATIONS

The present application is the national stage entry of International Patent Application No. PCT/EP2016/078247, filed on Nov. 21, 2016, and claims priority to Application No. EP 15196675.1, filed on Nov. 27, 2015, the disclosures of which are incorporated herein by reference.

TECHNICAL FIELD

The present disclosure relates to an injection device.

BACKGROUND

Injection devices, such as auto-injectors, are known in the art for dispensing a medicament to the injection site of a patient. Such injection devices typically comprise a body and a cap. A needle syringe is located in the body. The cap is removably attached to the body to shield the needle of the needle syringe. To dispense the medicament, the cap is first removed from the body to expose the needle. The needle is then inserted into the body of the patient at the injection site to dispense the medicament.

It may be important that the cap is held onto the body with sufficient force to ensure that the cap is not accidentally removed from the body during transport and storage of the injection device. This ensures that the needle is kept sterile and also prevents the sharp needle from causing injury. However, the force required to hold the cap and body together can make it difficult for the patient to intentionally remove the cap from the body prior to injection, particularly if the patient is elderly or infirm.

SUMMARY

Certain aspects of the present disclosure can be implemented to provide an improved injection device.

According to the present disclosure, there is provided a body for holding a syringe having a needle at one end thereof; a cap that is removably attached to the body and has a needle shield to cover said needle; a biasing member that is configured to urge at least a part of the cap away from the body; and, a lock that is moveable between a locked state, wherein the lock holds the cap and body together, and an unlocked state, wherein the cap and body are able to move apart. The biasing member facilitates removal of the cap from the body and the lock allows the patient to control when the cap is removed from the body.

In one embodiment, the biasing member is configured to urge the entire cap away from the body when the lock is in the locked state. Therefore, the cap may be completely removed from the body when the lock is moved from the locked state to the unlocked state.

The lock may comprise a spring and, preferably, a helical spring. The spring may have a steep spring characteristic curve. This helps to ensure that the biasing force of the spring is sufficient to overcome frictional forces between the cap and the body to urge the cap away from the body when the lock is moved from the locked state to the unlocked state, whilst a smaller biasing force is exerted by the spring when it is extended.

In an alternative embodiment, the biasing member comprises a hydraulic actuator or pneumatic actuator.

In one embodiment, the lock comprises a latch or bayonet connection. The cap may be moveable relative to the body to move the lock from the locked state to the unlocked state. Therefore, the cap must be twisted relative to the body to move the lock to the unlocked state and so the likelihood of accidental removal of the cap from the body is reduced. In one such embodiment, the cap is rotatable relative to the body to move the lock from the locked state to the unlocked state.

In one embodiment, the cap is moveable relative to the body in a first direction to move the lock from the locked state to an intermediate state, and the cap is movable relative to the body in a second direction that is different to the first direction to move the lock from the intermediate state to the unlocked state. Therefore, the cap must be moved relative to the body in two different directions to move the lock from the locked state to the unlocked state and therefore the likelihood of accidental removal of the cap from the body is reduced.

In one embodiment, the lock comprises a track on one of the body and cap and a pin on the other one of the body and cap, wherein the pin is configured to be received in the track. The track may extends non-linearly. The track may be generally U-shaped.

In one embodiment, the injection device comprises a projection in the track that is configured to resist movement of the pin in the track. Therefore, accidental movement of the pin in the track may be prevented, thereby reducing the likelihood that the cap is unintentionally removed from the body. In one such embodiment, the injection device further comprises a button that is coupled to the projection. The button may be arranged such that it may be pressed by the user to push the projection into the body to facilitate movement of the pin in the track.

The injection device may further comprise a needle sleeve, wherein the needle sleeve is moveable relative to the body between an extended position, to shield said needle when a syringe is held within the body, and a retracted position, wherein said needle extends axially past an end of the needle sleeve, wherein the needle sleeve moves to the extended position when the lock is in the unlocked state and the cap is removed from the body. The needle sleeve prevents accidental injury to the patient when the cap has been removed from the body. In one embodiment, the needle sleeve is biased into the extended position by the biasing member. The cost, weight, and complexity of the injector device is therefore reduced because the same biasing member is used to urge the cap away from the body and to urge the needle sleeve into the extended position.

In one embodiment, the needle sleeve is configured such that when the needle sleeve is moved from the retracted position to the extended position the needle sleeve exerts a force on the cap to urge said at least a part of the cap away from the body.

The lock may be configured such that when the cap is attached to the body the needle sleeve is urged into the body. Therefore, the length of the injector device can be reduced in comparison to an arrangement wherein the needle sleeve is in the extended position when the cap is attached to the body and the lock is in the locked state. In one embodiment, the lock is configured such that when the cap is attached to the body and the lock is in the locked state the needle sleeve is held in the retracted position.

In one embodiment, the body comprises a first stop and the needle sleeve comprises a second stop that is configured to engage with the first stop when the needle sleeve is in the extended position to limit the range of axial movement between the needle sleeve and the body. Therefore, the needle sleeve is prevented from becoming separated from the body when the needle sleeve moves from the retracted position to the extended position.

In one embodiment, the cap comprises a flange, and wherein the biasing member is disposed between the flange and a portion of the body when the cap is attached to the body.

In one embodiment, the cap and body engage such that there is a friction force therebetween that resists the cap and body moving apart, wherein the biasing force of the biasing member is greater than the friction force such that when the lock is moved to the unlocked state the cap and body move apart. In an alternative embodiment, the cap and body engage such that there is a friction force therebetween that resists the cap and body moving apart, and wherein the biasing force of the biasing member is less than the friction force.

The injection device may comprise a syringe that has a needle at one end and is received in the body. The needle shield may be in frictional engagement with the syringe. The syringe may contain a medicament.

In one embodiment, the injection device is an auto-injector.

According to the present disclosure, there is also provided a method of removing a cap from an end of a body of an injection device, comprising the steps of: rotating the cap about a longitudinal axis of the body, wherein the cap is held in place against the force of a biasing member by a lock prior to rotation of the cap; removing the cap from the end of the body, wherein the cap is urged away from the body by the force of the biasing member; and, extending a needle shield from said end of the body. The injection device may comprise one or more of the features of the injection device described hereinbefore.

These and other aspects of the disclosure will be apparent from and elucidated with reference to the embodiments described hereinafter.

BRIEF DESCRIPTION OF THE DRAWINGS

Embodiments of the disclosure will now be described, by way of example only, with reference to the accompanying drawings, in which:

FIG. 2 is a schematic cross-sectional side view of an injection device according to a first embodiment of the disclosure, wherein a cap is attached to a body of the injection device;

FIG. 3 is a schematic cross-sectional side view of the injection device of FIG. 2, wherein the cap is separated from the body;

FIG. 4 is a schematic cross-sectional side view of an injection device according to a second embodiment of the disclosure, wherein a cap is attached to a body of the injection device; and, FIG. 5 is a schematic cross-sectional side view of the injection device of FIG. 4, wherein the cap is separated from the body;

DETAILED DESCRIPTION

Figure 1A:
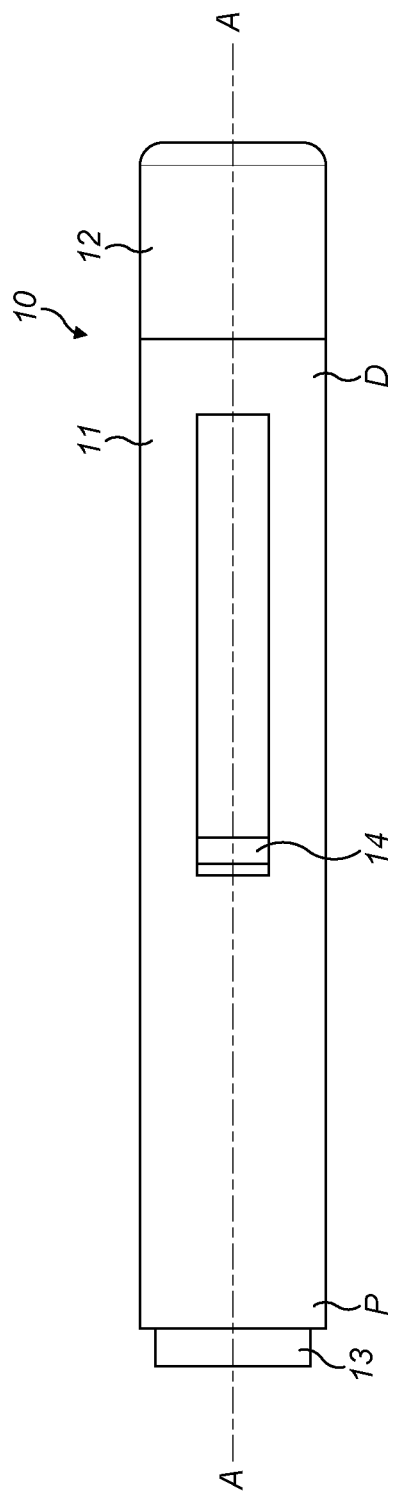
FIG. 1A is a schematic side view of an injection device, with a cap attached to a body of the injection device.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device may often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
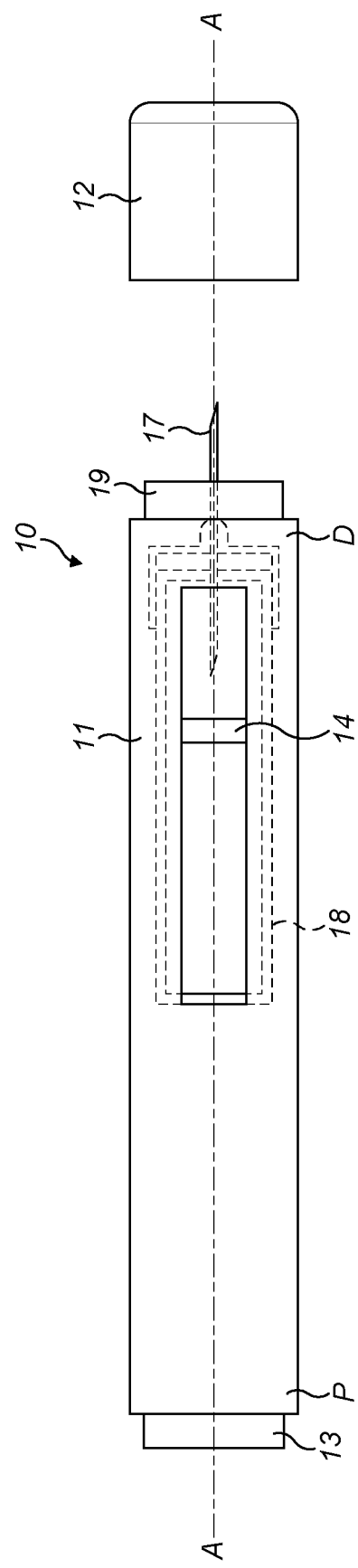
FIG. 1B is a schematic side view of the injection device of FIG. 1A, with the cap removed from the body.
Figure 6:
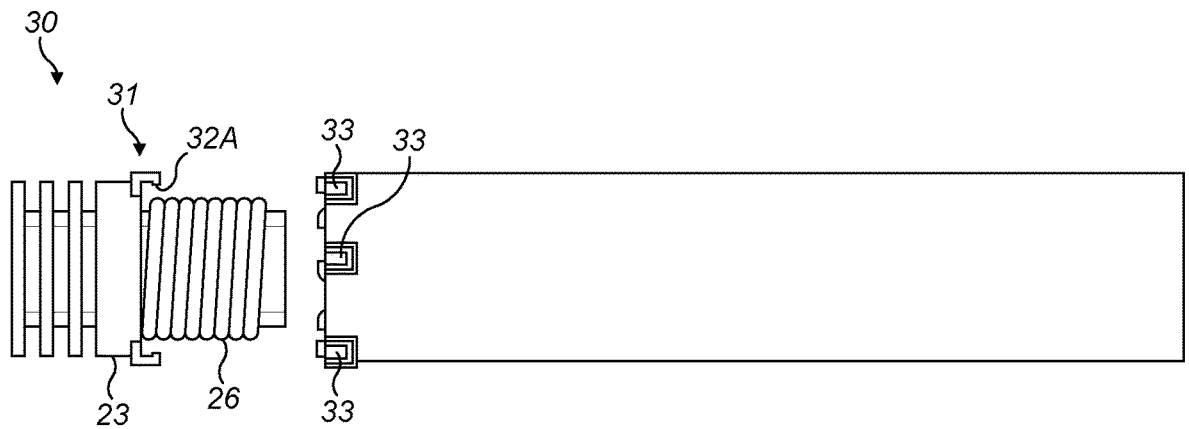
FIG. 6 is a schematic side view of the injection device of FIG. 4, wherein the cap is separated from the body.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated," whereby needle 17 moves relative to housing 11. Such insertion can be triggered by movement of sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location within a syringe 18 to a more distal location within the syringe 18 in order to force a medicament from the syringe 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the syringe 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the syringe 18 within housing 11 is moved in a proximal direction relative to housing 11. This proximal movement can be achieved by using a retraction spring (not shown), located in distal region D. A compressed retraction spring, when activated, can supply sufficient force to the syringe 18 to move it in a proximal direction. Following sufficient retraction, any relative movement between needle 17 and housing 11 can be locked with a locking mechanism. In addition, button 13 or other components of device 10 can be locked as required.

Referring now to FIGS. 2 and 3, an injection device 20 according to a first embodiment of the disclosure is shown. The injection device 20 is in the form of an auto-injector 20 that has similar features to the auto-injector 10 described above in relation to FIGS. 1A and 1B, with like features retaining the same reference numerals. A difference is that the cap 12 of the auto-injector 10 described above is omitted and is replaced with an alternative cap 21.

The cap 21 of the auto-injector 20 of the first embodiment of the disclosure comprises a needle shield 22 and an outer cap 23. The outer cap 23 comprises a tubular portion 24 with a flange 25 at one end. The needle shield 22 is received within the tubular portion 24 of the outer cap 23 and is fixed thereto.

The cap 21 is removably attachable to the body 11 such that the tubular portion 24 of the outer cap 23 is received in the open distal end 11A of the body 11 and the flange 25 abuts the open distal end 11A (as shown in FIG. 2). When the cap 21 is in this position, the needle shield 22 receives the needle 17 such that the needle 17 is shielded to prevent contamination of the needle 17 or injury to the patient.

The cap 21 further comprises a biasing member 26 and a lock 27. The biasing member 26 is in the form of a helical spring 26. The spring 26 is located on the outside of the tubular portion 24 such that the spring 26 extends about the central axis A-A of the auto-injector 20.

The body 11 comprises an annular internal shoulder 11B that extends radially from the peripheral wall of the body 11 towards the central axis A-A of the auto-injector 20. The spring 26 is compressed between the internal shoulder 11B of the body 11 and the flange 25 of the outer cap 23 when the needle 17 is received in the needle shield 22. Therefore, the spring 26 biases the outer cap 23 away from the body 11 when the cap 21 is attached to the body 11 (in the direction of arrow 'F' shown in FIG. 2).

The lock 27 is in the form of a latch. The lock 27 comprises first and second locking members 28, 29. The first locking member 28 extends from the flange 25 of the outer cap 23. The first locking member 28 is arranged to extend towards the proximal end P of the auto-injector 20 when the cap 21 is received on the body 11 and comprises a recess 28A. The second locking member 29 extends radially from the outside of the peripheral wall of the body 11 and is disposed at the open peripheral end 11A of the body 11.

The outer cap 23 is configured to be rotated relative to the body 11 about the central axis A-A of the auto-injector 20 to move the lock 27 between a locked state and an unlocked state. When the lock 27 is in the locked state, the first and second locking members 28, 29 engage such that part of the second locking member 29 is received in the recess 28A of the first locking member 28 to prevent the cap 21 from moving axially relative to the body 11 (as shown in FIG. 2). To move the lock 27 to the unlocked state, the outer cap 23 is twisted relative to the body 11 to disengage the first and second locking members 28, 29 such that the second locking member 29 is no longer received in the recess 28A of the first locking member 28. When the first and second locking members 28, 29 are disengaged the cap 21 can be moved axially away from the body 11.

The cap 21 is initially attached to the body 11 such that the needle 17 is completely received in the needle shield 22 and the lock 27 is in the locked state (as shown in FIG. 2) to hold the cap 21 in position on the body 11 against the force of the spring 26. Thus, the needle 17 is covered by the needle shield 22 to keep the needle 17 sterile and to prevent the needle 17 from causing injury to the patient.

To inject medicament, the cap 21 is first removed from the body 11 to expose the needle 17. Removal of the cap 21 from the body 11 is achieved by the patient exerting a force on the flange 25 of the outer cap 23 to twist the outer cap 23 relative to the body 11 about the central axis A-A of the auto-injector 20 such that the lock 27 moves from the locked state to the unlocked state. This causes the first and second locking members 28, 29 to disengage such that the outer cap 23 is axially moveable relative to the body 11. Therefore, the lock 27 no longer holds the cap 21 in position on the body 11 against the biasing force of the spring 26 and so the biasing force of the spring 26 moves the outer cap 23 away from the body 11 (in the direction of arrow 'F' shown in FIG. 2).

The needle shield 22, which is axially fixed relative to the outer cap 23, is therefore also moved away from the body 11 until the needle 17 is no longer received in the needle shield 22 and the cap 21 is separated from the body 11 (as shown in FIG. 3).

With the cap 21 removed from the body 11, the open distal end 11A of the body 11 is pressed up against an injection site of the patient. The dispense button (not shown) is then pressed to cause the dispense mechanism (not shown) to move the needle 17 towards the injection site and to dispense medicament to the injection site. In an alternative embodiment (not shown), the injection device 20 is configured such that needle 17 moves towards the injection site automatically and/or medicament is dispensed automatically when the open distal end 11A of the body 11 is pressed up against an injection site of the patient.

The biasing member 26 and lock 27 therefore makes it easier for the patient to remove the cap 21 from the body 11. This is because the patient only needs to exert enough force on the outer cap 23 to twist the outer cap 23 to move the lock 27 from the locked state to the unlocked state. The biasing force of the biasing member 26 then overcomes the friction between the cap 21 and the body 11 and needle 17 to separate the needle shield 22 from the needle 17. The force required to move the lock 27 to the unlocked state may be significantly lower than the force necessary to overcome the friction between the cap 21 and the body 11 and needle 17. Furthermore, the twisting motion required to remove the cap 21 from the body 11 makes accidental removal of the cap 21 less likely.

Referring now to FIGS. 4 to 7C, an injection device 30 according to a second embodiment of the disclosure is shown. The injection device 30 is in the form of an auto-injector 30 that has similar features to the auto-injector 20 described above in relation to the first embodiment of the disclosure shown in FIGS. 2 and 3, with like features retaining the same reference numerals. A difference is that the lock 27 of the cap 21 of the first embodiment is omitted and is replaced with an alternative lock.

The lock is in the form of a plurality of bayonet connections 31. The bayonet connections 31 are spaced about the central axis A-A of the auto-injector 30. Each bayonet connection 31 comprises a locking member 32 and a track 33. The locking members 32 extend from the flange 25 of the outer cap 23. The locking members 32 extend axially towards the proximal end of the needle shield 22. The end of each locking member 32 comprises a pin 32A that extends radially inwardly towards the central axis A-A of the auto-injector 30.

Each track 33 is formed in the peripheral surface of the body 11 and is non-linear. More specifically, each track 33 is generally U-shaped. The tracks 33 are configured to each receive the pin 32A of a corresponding locking member 32 when the cap 21 is attached to the body 11.

Each track 33 has first, second and third track portions 33A, 33B, 33C. The first track portion 33A extends axially from the open distal end 11A of the body 11 towards the proximal end P of the auto-injector 30. The second track portion 33B extends circumferentially from an end of the first track portion 33A. The third track portion 33C extends axially from the opposite end of the second track portion 33B to the first track portion 33A. The third track portion 33C extends towards the open distal end 11A of the body 11, but terminates before the open distal end 11A.

The outer cap 23 is configured to be moved relative to the body 11 to move the lock between a locked state and an unlocked state. More specifically, the outer cap 23 is moved relative to the body 11 to move each bayonet connection 31 between a locked state (shown in FIG. 7A) and an unlocked state (shown in FIG. 7C).

Figure 7A:
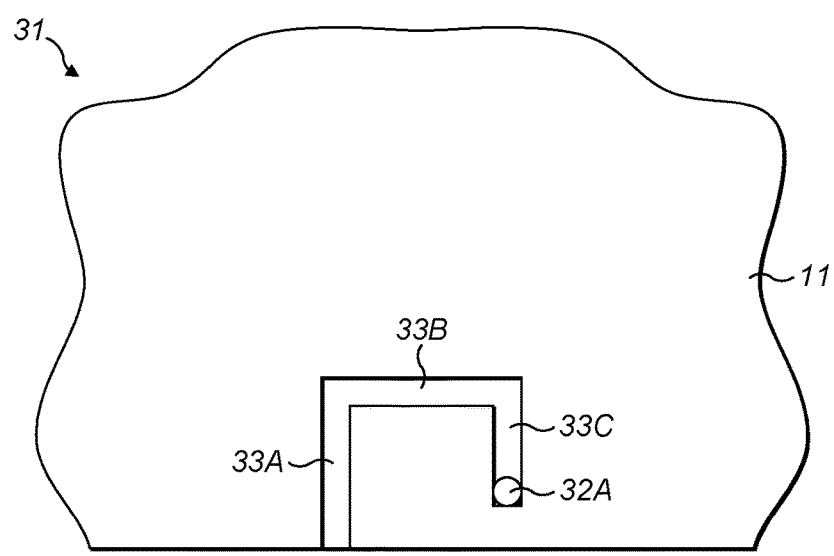
FIG. 7A is a schematic close-up view of a part of a lock of the injection device of FIG. 4, wherein the lock is in a locked state.

When each bayonet connection 31 is in the locked state, the pin 32A of each locking member 32 is received in a corresponding third track portion 33C (as shown in FIG. 7A) such that the biasing force of the biasing member 26 urges each pin 32A against the nearest end of the third track portion 33C to the open distal end 11A of the body 11. Thus, the cap 21 is prevented from moving axially away from the body 11.

Figure 7B:
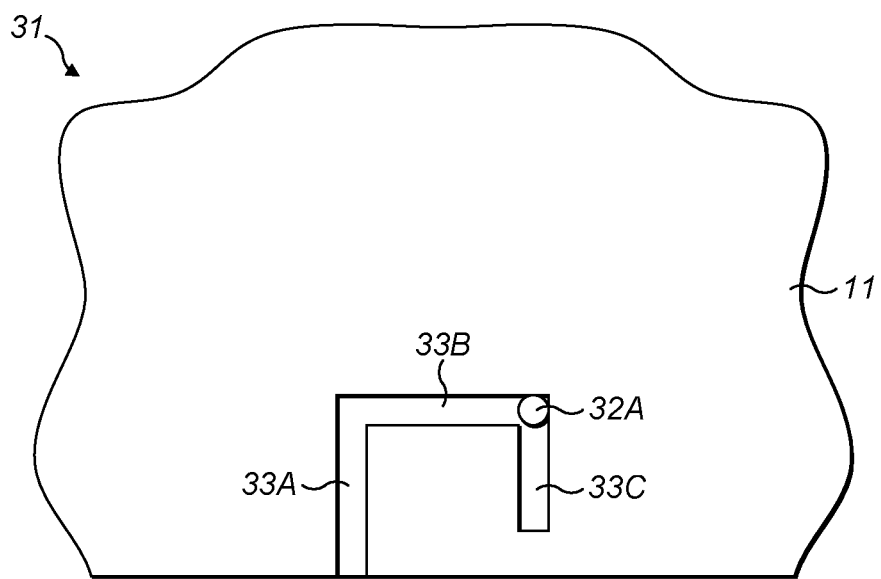
FIG. 7B is a schematic close-up view of a part of the lock of the injection device of FIG. 4, wherein the lock is in an intermediate state.

To move each bayonet connection 31 to the unlocked state, the outer cap 23 is urged axially towards the body 11 to move the pin 32A of each locking member 32 axially away from the open distal end 11A of the body 11. This causes, the lock, and more specifically each bayonet connection 31, to move to an intermediate state (as shown in FIG. 7B), wherein each pin 32A moves along the corresponding third track portion 33C and into an end of the corresponding second track portion 33B. In the intermediate state, the pins 32A engage with the walls of the corresponding second track portions 33B such that the lock prevents the outer cap 23 from being moved axially relative to the body 11.

With the lock in the intermediate state, the outer cap 23 is then twisted relative to the body 11 to move the pin 32A of each locking member 32 circumferentially relative to the body 11. This causes the lock to move from the intermediate state to the unlocked state, wherein each pin 32A moves along the respective second track portion 33B and into an end of a corresponding first track portion 33A that is distal to the open distal end 11A of the body 11. When the lock is in the unlocked state the outer cap 23 is able to move axially relative to the body 11 such that the biasing force of the biasing member 26 moves the cap 21 away from the body 11.

The cap 21 is initially attached to the body 11 such that the needle 17 is completely received in the needle shield 22 (as shown in FIG. 4) and the lock is in the locked state to hold the cap 21 in position on the body 11 against the force of the biasing member 26. Thus, the needle 17 is covered by the needle shield 22 to keep the needle 17 sterile and to prevent the needle 17 from causing injury to the patient.

To inject medicament, the cap 21 is first removed from the body 11 to expose the needle 17. Removal of the cap 21 from the body 11 is achieved by the patient exerting a force on the outer cap 23 to press the outer cap 23 axially towards the body 11 (in the opposite direction to arrow 'F' in FIG. 4) against the biasing force of the biasing member 26 such that the lock, and more specifically each bayonet connection 31, moves to the intermediate state (as shown in FIG. 7B).

Figure 7C:
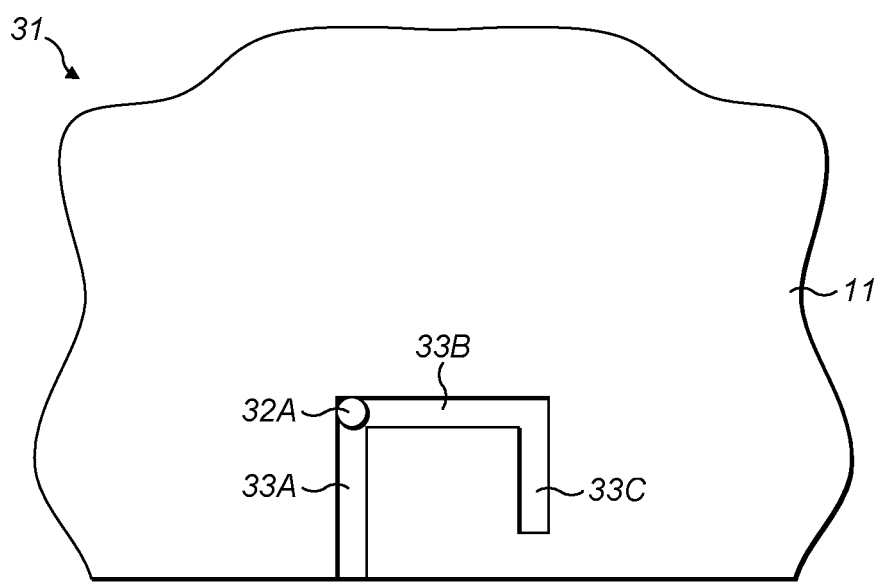
FIG. 7C is a schematic close-up view of a part of the lock of the injection device of FIG. 4, wherein the lock is in an unlocked state.

The patient then twists the outer cap 23 relative to the body 11 to move the lock from the intermediate state to the unlocked state (as shown in FIG. 7C). In the unlocked state, each bayonet connection 31 of the lock no longer holds the cap 21 in position on the body 11 against the biasing force of the biasing member 26 and so the biasing force moves the outer cap 23 away from the body 11 (in the direction of arrow 'F' shown in FIG. 4).

The needle shield 22, which is axially fixed relative to the outer cap 23, is therefore moved away from the body 11 when the lock is moved from the intermediate state to the unlocked state, until the needle 17 is no longer received in the needle shield 22 and the cap 21 is separated from the body 11 (as shown in FIG. 5).

With the cap 21 removed from the body 11, the open distal end 11A of the body 11 is pressed up against an injection site of the patient. The dispense button (not shown) is then pressed to cause the dispense mechanism (not shown) to move the needle 17 towards the injection site and to dispense medicament to the injection site. In an alternative embodiment (not shown), the injection device 30 is configured such that needle 17 moves towards the injection site automatically and/or medicament is dispensed automatically when the open distal end 11A of the body 11 is pressed up against an injection site of the patient.

The biasing member 26 and lock therefore makes it easier for the patient to remove the cap 21 from the body 11. This is because the patient only needs to move the outer cap 23 towards to the body 11 by a small amount, to move the lock to the intermediate state, and then to twist the outer cap 23 relative to the body 11 to move the lock from the intermediate state to the unlocked state. The biasing force of the biasing member 26 is sufficient to overcome the friction between the cap 21 and the body 11 and needle 17 in order to separate the cap 21 from the body 11. Furthermore, since the cap 21 must be moved in two different directions to move the lock from the locked state to the unlocked state, namely first moved axially towards the body 11 and then rotated relative to the body 11, accidental removal of the cap 21 from the body 11 is less likely. For example, if the outer cap 23 was accidentally pressed towards the body 11 to move the lock to the intermediate state, then the biasing member 26 would urge the outer cap 23 back away from the body 11 such that the lock moves back to the locked state.

Although in the above described second embodiment the locking members 32 extend from the outer cap 23 and the tracks 33 are formed in the body 11, in an alternative embodiment (not shown) the locking members extend from the body and the tracks are formed in the outer cap. Although in the above described second embodiment the lock comprises a plurality of bayonet connections 31, in an alternative embodiment (not shown) the lock comprises a single bayonet connection.

Although in the above described first and second embodiment the lock is on the outside of the body 11 and outer cap 23, in alternative embodiments (not shown) the lock is on the inside of the body and outer cap.

In the above described first and second embodiments the biasing member 26 is urged against the outer cap 23 to urge the cap 21 away from the body 11. However, in alternative embodiments (not shown) the biasing member is instead arranged to be urged against another part of the cap. In one such alternative embodiment, the biasing member is compressed between the needle shield and the body when the cap is attached to the body such that the biasing member is urged against the needle shield to urge the cap axially away from the body.

In the above described first and second embodiments, the biasing force of the biasing member 26 is sufficiently large to cause the cap 21 to be completely separated from the body 11 when the lock 27 is moved from the locked state to the unlocked state. In an alternative embodiment (not shown), the biasing force exerted on the outer cap 23 by the biasing member 26 is smaller than the frictional force holding the cap 21 on the body 11. Therefore, when the lock 27 is moved from the locked state to the unlocked state, the outer cap 23 does not move axially away from the body 11. However, the force of the biasing member 26 acting on the outer cap 23 reduces the force that must be exerted by the patient to remove the cap 21 from the body 11.

Figure 8A:
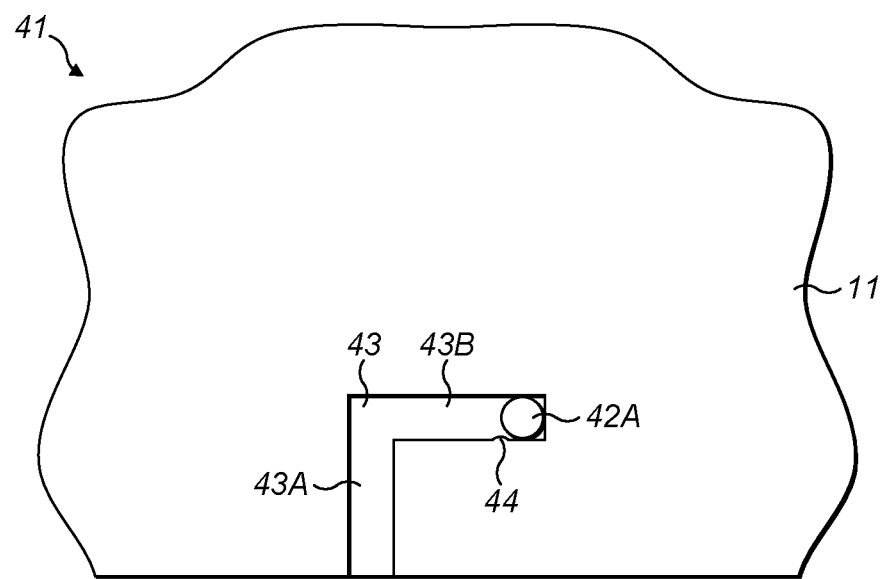
FIG. 8A is a schematic close-up view of a part of a lock of an injection device according to a third embodiment of the disclosure, wherein the lock is in a locked state.
Figure 8B:
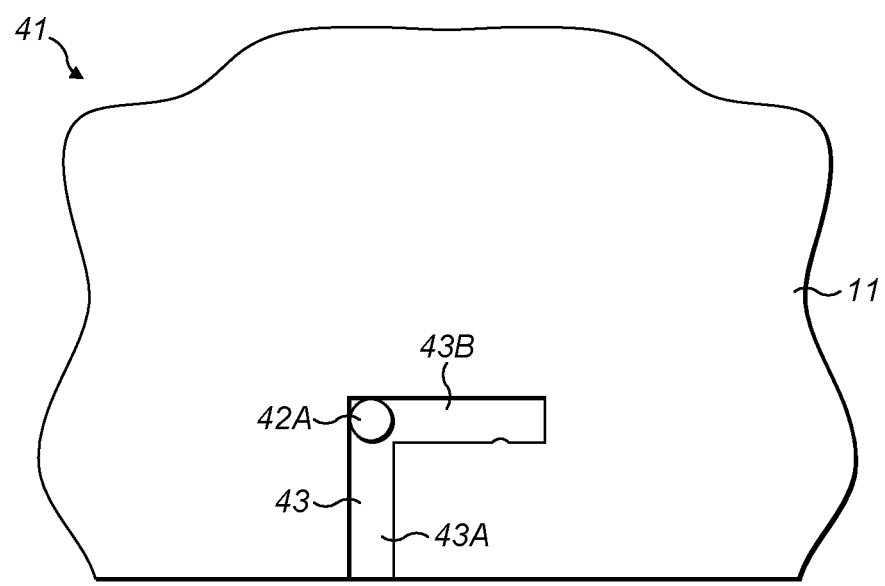
FIG. 8B is a schematic close-up view of a part of a lock of FIG. 8A, wherein the lock is in an unlocked state.

Referring now to FIGS. 8A and 8B, a part of an injection device according to a third embodiment of the disclosure is shown. The injection device is in the form of an auto-injector that has similar features to the auto-injector 30 described above in relation to FIGS. 4 to 7C, with like features retaining the same reference numerals. A difference is that the bayonet connections 31 of the lock are omitted and are replaced with alternative bayonet connections 41.

The bayonet connections 41 are spaced about the central axis of the auto-injector. Each bayonet connection 41 comprises a locking member (not shown) that has a pin 42A which extends radially inwardly towards the central axis of the auto-injector, similarly to the bayonet connections 31 of the auto-injector 30 shown in FIGS. 4 to 7C.

The bayonet connections 41 each comprise a track 43. Each track 43 is formed in the peripheral surface of the body 11 and is non-linear. More specifically, each track 43 is generally L-shaped. The tracks 43 are configured to each receive the pin 42A of a corresponding locking member when the cap is attached to the body 11.

Each track 43 has first and second track portions 43A, 43B. The first track portion 43A extends axially from the open distal end of the body 11 towards the proximal end of the auto-injector. The second track portion 33B extends circumferentially from an end of the first track portion 43A. The track 43 further comprises a projection 44 which projects into the second track portion 43B and is disposed towards an end thereof that is distal to the first track portion 43A.

The outer cap is configured to be moved relative to the body 11 to move each bayonet connection 41 between a locked state (shown in FIG. 8A) and an unlocked state (shown in FIG. 8B).

When each bayonet connection 41 is in the locked state, the pin 42A of each locking member is received in a corresponding second track portion 43B (as shown in FIG. 8A) such that the biasing force of the biasing member urges each pin 42A against an edge of the second track portion 43B. Thus, the cap is prevented from moving axially away from the body 11. Furthermore, when the bayonet connection 41 is in the locked state, the pin 42A of each locking member abuts a respective projection 44 such that the pin 42A is prevented from moving in the second track portion 43B. Thus, the projections 44 resist rotational movement between the cap and body 11 to prevent the cap from accidentally being removed from the body 11.

To move each bayonet connection 41 to the unlocked state, the outer cap is twisted relative to the body 11 to urge the pin 42A of each locking member past the corresponding projection 44 such that each pin 42A is moved circumferentially relative to the body 11. This causes the lock to move from the locked state to the unlocked state, wherein each pin 42A moves along the respective second track portion 43B and into an end of a corresponding first track portion 43A that is distal to the open distal end of the body 11. When the lock is in the unlocked state the outer cap is able to move axially relative to the body 11 such that the biasing force of the biasing member moves the cap away from the body 11.

Thus, the patient is able to twist the outer cap relative to the body 11 to move the lock from the locked state (shown in FIG. 8A) to the unlocked state (as shown in FIG. 8B), wherein the biasing force of the spring moves the outer cap away from the body 11 until the needle is no longer received in the needle shield and the cap is separated from the body 11.

Figure 9A:
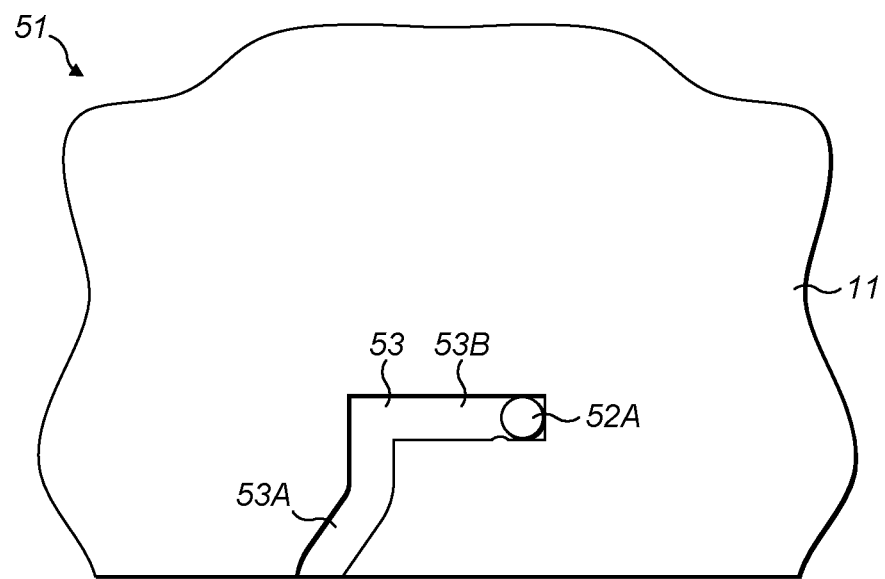
FIG. 9A is a schematic close-up view of a part of a lock of an injection device according to a fourth embodiment of the disclosure, wherein the lock is in a locked state.
Figure 9B:
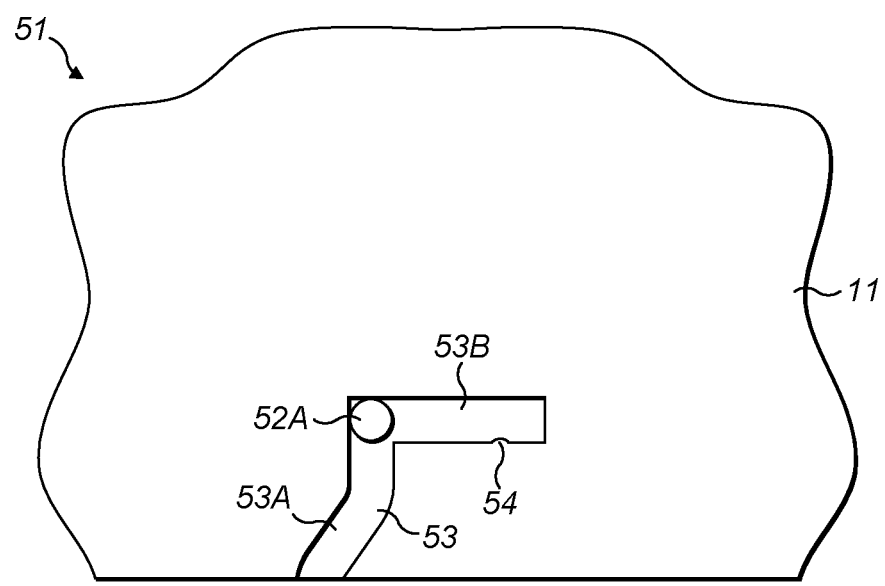
FIG. 9B is a schematic close-up view of a part of a lock of FIG. 9A, wherein the lock is in an unlocked state.

Referring now to FIGS. 9A and 9B, a part of an injection device according to a fourth embodiment of the disclosure is shown. The injection device is in the form of an auto-injector that has similar features to the auto-injector 30 described above in relation to FIGS. 4 to 7C, with like features retaining the same reference numerals. A difference is that the bayonet connections 31 of the lock are omitted and are replaced with alternative bayonet connections 51.

The bayonet connections 51 are spaced about the central axis of the auto-injector. Each bayonet connection 51 comprises a locking member (not shown) that has a pin 52A which extends radially inwardly towards the central axis of the auto-injector, similarly to the bayonet connections 31 of the auto-injector 30 shown in FIGS. 4 to 7C.

The bayonet connections 51 each comprise a track 53. Each track 53 is formed in the peripheral surface of the body 11 and is non-linear, having a generally L-shaped portion. The tracks 53 are configured to each receive the pin 52A of a corresponding locking member when the cap is attached to the body 11.

Each track 53 has first and second track portions 53A, 53B. The first track portion 53A extends from the open distal end of the body 11 towards the proximal end of the auto-injector. The first track portion 53A comprises a portion which extends at an angle to the central axis of the auto-injector. The second track portion 53B extends circumferentially from an end of the first track portion 53A. The track 53 further comprises a projection 54 which projects into the second track portion 53B and is disposed towards an end thereof that is distal to the first track portion 53A.

The outer cap is configured to be moved relative to the body 11 to move each bayonet connection 51 between a locked state (shown in FIG. 9A) and an unlocked state (shown in FIG. 9B).

When each bayonet connection 51 is in the locked state, the pin 52A of each locking member is received in a corresponding second track portion 53B (as shown in FIG. 9A) such that the biasing force of the biasing member urges each pin 52A against an edge of the second track portion 53B. Thus, the cap is prevented from moving axially away from the body 11. Furthermore, when the bayonet connection 51 is in the locked state, the pin 52A of each locking member abuts a respective projection 54 such that the pin 52A is prevented from moving in the second track portion 53B. Thus, the projections 54 resist rotational movement between the cap and body 11 to prevent the cap from accidentally being removed from the body 11.

To move each bayonet connection 51 to the unlocked state, the outer cap is twisted relative to the body 11 to urge the pin 52A of each locking member past the corresponding projection 54 such that each pin 52A is moved circumferentially relative to the body 11. This causes the lock to move from the locked state to the unlocked state, wherein each pin 52A moves along the respective second track portion 53B and into an end of a corresponding first track portion 53A that is distal to the open distal end of the body 11.

When the lock is in the unlocked state the outer cap is able to move axially relative to the body 11 such that the biasing force of the biasing member moves the cap away from the body 11. However, since the first track portion 53A extends at an angle to the central axis of the auto-injector, the cap must rotate relative to the body 11 as the pin 52A is moves axially relative to the body 11 along the first track portion 53A. Since the cap must rotate relative to the body 11 as it moves away from the body 11, the cap moves axially away from the body 11 at a slower rate under the force of the spring when the bayonet connections are moved from the locked state to the unlocked state and so a more controlled removal of the cap from the body 11 is achieved.

Thus, the patient is able to twist the outer cap relative to the body 11 to move the lock from the locked state to the unlocked state, wherein the biasing force of the spring moves the outer cap away from the body 11 until the needle is no longer received in the needle shield and the cap is separated from the body 11.

Referring now to FIGS. 10A to 10D, a part of an injection device according to a fifth embodiment of the disclosure is shown. The injection device is in the form of an auto-injector that has similar features to the auto-injector 30 described above in relation to FIGS. 4 to 7C, with like features retaining the same reference numerals. A difference is that the bayonet connections 31 of the lock are omitted and are replaced with alternative bayonet connections 61.

The bayonet connections 61 are spaced about the central axis of the auto-injector. Each bayonet connection 61 comprises a locking member (not shown) that has a pin 62A which extends radially inwardly towards the central axis of the auto-injector, similarly to the bayonet connections 31 of the auto-injector 30 shown in FIGS. 4 to 7C.

The bayonet connections 61 each comprise a track 63. Each track 63 is formed in the peripheral surface of the body 11. The tracks 63 are configured to each receive the pin 62A of a corresponding locking member when the cap is attached to the body 11.

Each track 63 is non-linear and has first, second, third and fourth track portions 63A, 63B, 63C and 63D. The first track portion 63A extends from the open distal end of the body 11 towards the proximal end of the auto-injector. The second track portion 63B extends circumferentially from an end of the first track portion 63A. The third track portion 63C extends axially away from the end of the second track portion 63B that is distal to the first track portion 63A and extends towards the proximal end of the auto-injector. The fourth track portion 63D extends circumferentially from the end of the third track portion 63C that is distal to the second track portion 63B.

The track 63 further comprises a projection 64 which projects into the fourth track portion 63D and is disposed towards an end thereof that is distal to the third track portion 63C.

Figure 10A:
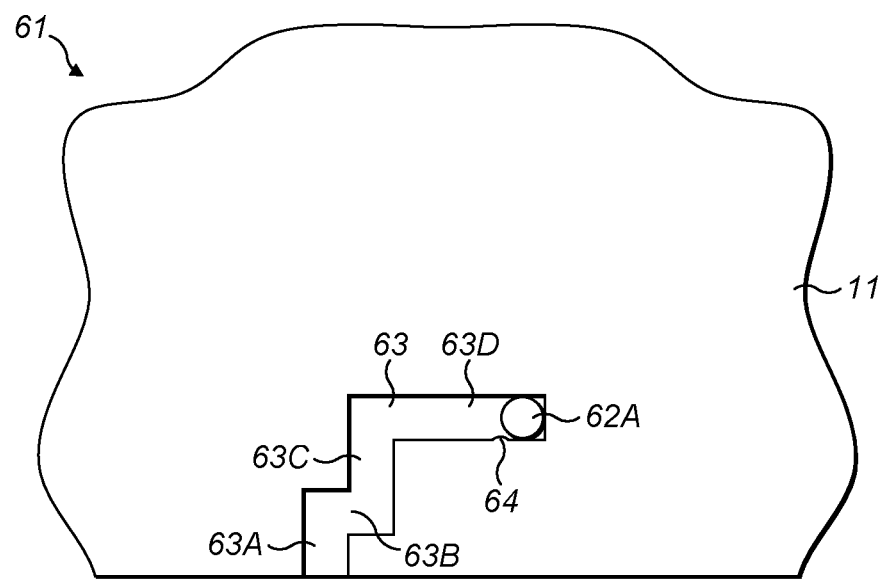
FIG. 10A is a schematic close-up view of a part of a lock of an injection device according to a fifth embodiment of the disclosure, wherein the lock is in a locked state.
Figure 10B:
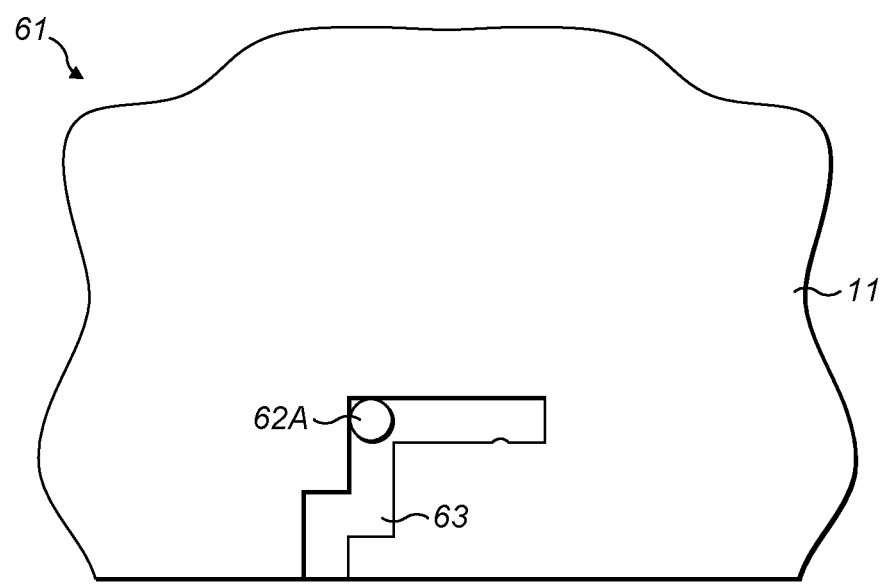
FIG. 10B is a schematic close-up view of a part of a lock of FIG. 10A, wherein the lock is in a first intermediate state.
Figure 10C:
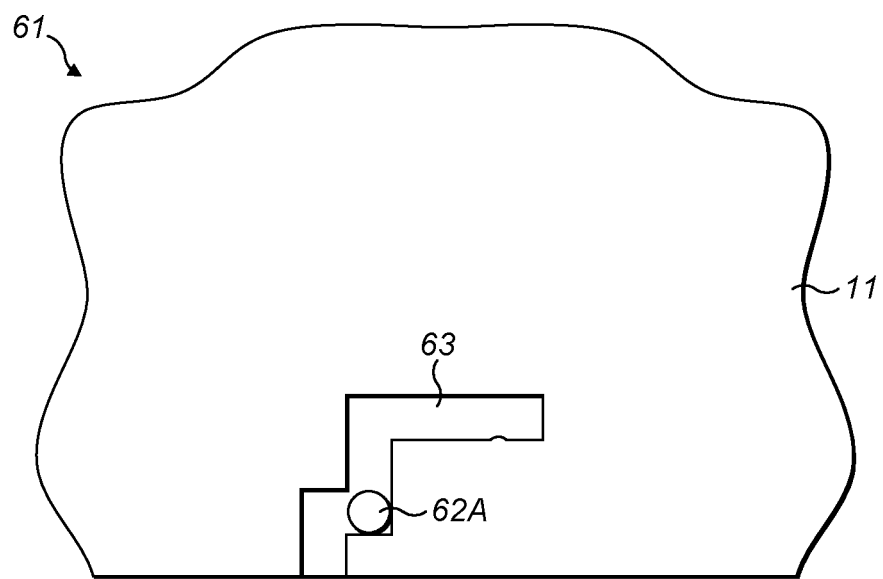
FIG. 10C is a schematic close-up view of a part of a lock of FIG. 10A, wherein the lock is in a second intermediate state.

The outer cap is configured to be moved relative to the body 11 to move each bayonet connection 61 between a locked state (shown in FIG. 10A) and an unlocked state (shown in FIG. 10D), via first and second intermediate states (shown in FIGS. 10B and 10C).

When each bayonet connection 61 is in the locked state, the pin 62A of each locking member is received in a corresponding fourth track portion 63D (as shown in FIG. 10A) such that the biasing force of the biasing member urges each pin 62A against an edge of the fourth track portion 63D. Thus, the cap is prevented from moving axially away from the body 11.

Furthermore, when the bayonet connection 61 is in the locked state, the pin 62A abuts the projection 64 such that the pin 62A is prevented from moving in the fourth track portion 63D. Thus, the projections 64 resist rotational movement between the cap and body 11 to prevent the cap from accidentally being removed from the body 11.

To move each bayonet connection 61 to the unlocked state, the outer cap is twisted relative to the body 11 to urge the pin 62A of each locking member past the corresponding projection 64 such that each pin 62A is moved circumferentially relative to the body 11. This causes the lock to move from the locked state to the first intermediate state, wherein each pin 62A moves along the respective fourth track portion 63D and into an end of a corresponding third track portion 63C that is distal to the open distal end of the body 11 (as shown in FIG. 10B).

When the lock is in the first intermediate state the outer cap is able to move axially relative to the body 11 such that the biasing force of the biasing member moves the cap axially away from the body 11. This causes each pin 62A to move within a corresponding third track portion 63C in the axial direction until the pin 62A is disposed in the end of the third track portion 63C that is proximate the second track portion 63B, wherein the lock is in the second intermediate state (as shown in FIG. 10C). The range of axial movement of the cap relative to the body 11 when the lock is moved from the first intermediate state to the second intermediate state is limited to the length of the third track portion 63C.

Figure 10D:
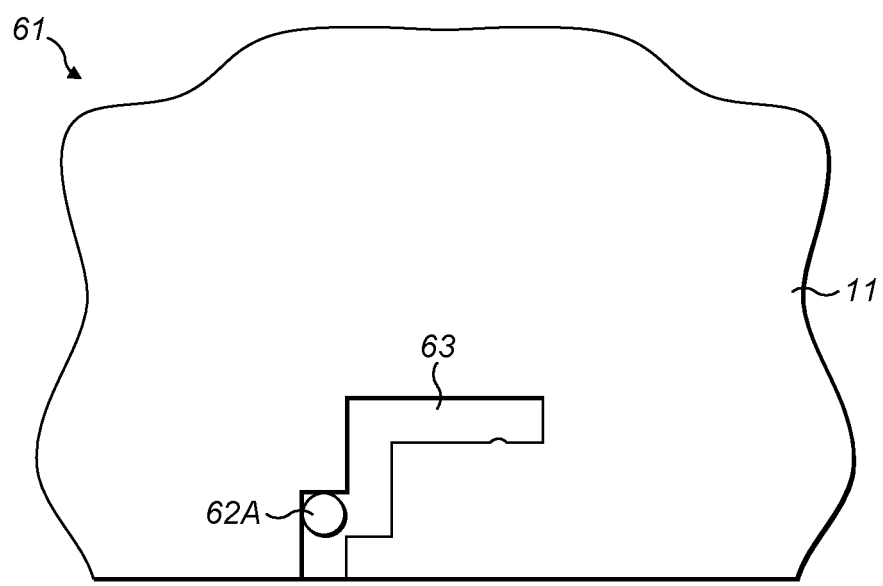
FIG. 10D is a schematic close-up view of a part of a lock of FIG. 10A, wherein the lock is in an unlocked state.

When the lock is in the second intermediate state the user is able to twist the outer cap to rotate the outer cap relative to the body 11. This causes each pin 62A to move within the corresponding second track portion 63B in the circumferential direction until the pin 62A is disposed at the end of the second track portion 63B that is proximate the first track portion 63A, wherein the lock is in the unlocked state (as shown in FIG. 10D).

When the lock is in the unlocked state the outer cap is able to move axially relative to the body 11 such that the biasing force of the biasing member moves the cap away from the body 11 to separate the cap from the body 11. Thus, the patient is able to twist the outer cap relative to the body 11 to move the lock from the locked state to the unlocked state, wherein the biasing force of the spring moves the outer cap away from the body 11 until the needle is no longer received in the needle shield and the cap is separated from the body 11.

Since the cap must be rotated relative to the body 11 in stages to separate the cap from the body 11, namely a first time to move the lock from the locked state to the first intermediate state and a second time to move the lock from the second intermediate state to the unlocked state, accidental removal of the cap from the body 11 is prevented. Furthermore, the removal of the cap from the body 11 in stages prevents the cap from being completely separated from the body 11 as soon as the lock is moved away from the locked state, thereby allowing for a more controlled removal of the cap from the body 11.

Figure 11A:
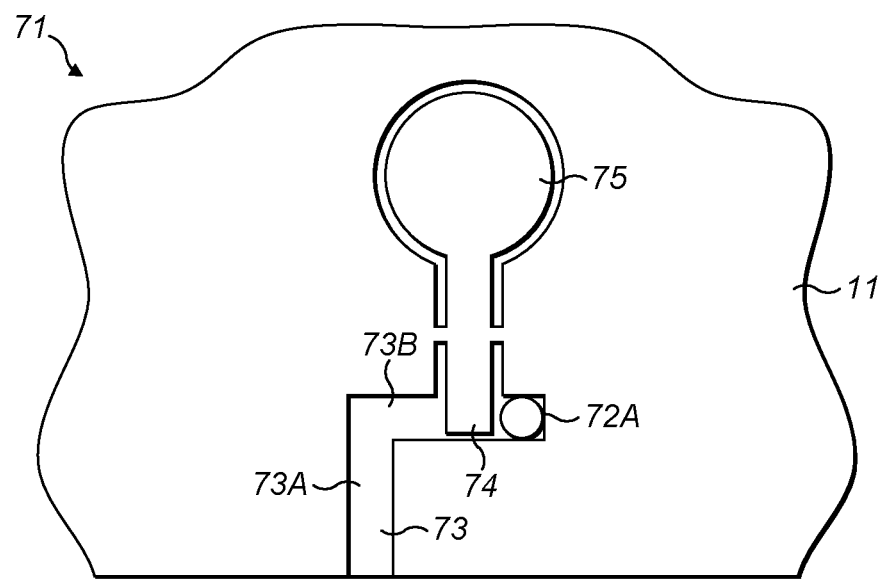
FIG. 11A is a schematic close-up view of a part of a lock of an injection device according to a sixth embodiment of the disclosure, wherein the lock is in a locked state.
Figure 11B:
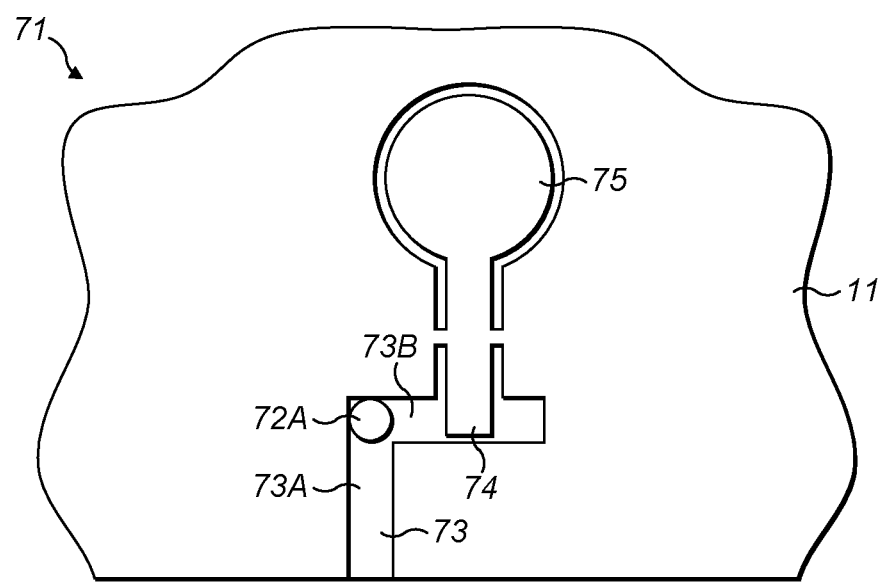
FIG. 11B is a schematic close-up view of a part of a lock of FIG. 11A, wherein the lock is in an unlocked state.

Referring now to FIGS. 11A and 11B, a part of an injection device according to a sixth embodiment of the disclosure is shown. The injection device is in the form of an auto-injector that has similar features to the auto-injector described above in relation to FIGS. 8A and 8B, with like features retaining the same reference numerals. A difference is that the bayonet connections 41 of the lock are omitted and are replaced with an alternative bayonet connection 71.

The bayonet connection 71 comprises a locking member (not shown) that has a pin 72A which extends radially inwardly towards the central axis of the auto-injector, similarly to the bayonet connections 41 of the auto-injector shown in FIGS. 8A and 8B. The bayonet connection 71 comprises a track 73 that is formed in the peripheral surface of the body 11 and is generally L-shaped. The track 73 is configured to receive the pin 72A of the locking member when the cap is attached to the body 11.

The track 73 is non-linear, having first and second track portions 73A, 73B. The first track portion 73A extends axially from the open distal end of the body 11 towards the proximal end of the auto-injector. The second track portion 73B extends circumferentially from an end of the first track portion 73A.

The track 73 further comprises a projection 74 which projects into the second track portion 73B and is disposed towards an end thereof that is distal to the first track portion 73A. The projection 74 is coupled to a button 75 that is configure to be resiliently urged into the body 11 such that the projection 74 is moved into the body 11 to sit flush to the surface of the second track portion 73B.

The outer cap is configured to be moved relative to the body 11 to move the bayonet connection 71 between a locked state (shown in FIG. 11A) and an unlocked state (shown in FIG. 11B).

When the bayonet connection 71 is in the locked state, the pin 72A of the locking member is received in the second track portion 73B (as shown in FIG. 11A) such that the biasing force of the biasing member urges the pin 72A against an edge of the second track portion 73B. Thus, the cap is prevented from moving axially away from the body 11. Furthermore, when the bayonet connection 71 is in the locked state, the pin 72A of the lock abuts the projection 74 such that the pin 72A is prevented from moving in the second track portion 73B. Thus, the projection 74 resists rotational movement between the cap and body 11 to prevent the cap from accidentally being removed from the body 11.

To move the bayonet connection 71 to the unlocked state, the user presses the button 75 into the body 11 such that the projection 74 is moved into the body 11 to sit flush to the surface of the second track portion 73B. Therefore, the projection 74 no longer resists rotational movement between the cap and body 11 and so the outer cap can be twisted relative to the body 11 to urge the pin 72A of the locking member over the projection 74 such that the pin 72A is moved circumferentially relative to the body 11. This causes the lock to move from the locked state to the unlocked state, wherein the pin 72A moves along the respective second track portion 73B and into an end of the first track portion 73A that is distal to the open distal end of the body 11. When the lock is in the unlocked state the outer cap is able to move axially relative to the body 11 such that the biasing force of the biasing member moves the cap away from the body 11 and the pin 72A moves axially within the first track portion 73A.

Thus, the patient is able to twist the outer cap relative to the body 11 to move the lock from the locked state (shown in FIG. 11A) to the unlocked state (shown in FIG. 11B), wherein the biasing force of the spring moves the outer cap away from the body 11 until the needle is no longer received in the needle shield and the cap is separated from the body 11.

In an alternative embodiment (not shown), the injection device comprises a plurality of bayonet connections 71 which are spaced about the central axis of the auto-injector. Each bayonet connection 71 comprises a pin 72A that is received in a corresponding track 73. Each track 73 comprises a corresponding projection 74 that is moved upon actuation of a respective button 75.

The bayonet connections 41, 51, 61, 71 described above in relation to FIGS. 8A to 11B provide the technical advantage of not requiring the user to axially move the end cap towards the body 11, against the force of the spring, to move the bayonet connections 41, 51, 61, 71 from the locked state to the unlocked state.

Referring now to FIGS. 12 to 17, an injection device 80 according to a seventh embodiment of the disclosure is shown. The injection device 80 is in the form of an auto-injector 80 that has similar features to the auto-injector 10 described above in relation to FIGS. 1A and 1B, with like features retaining the same reference numerals. A difference is that the cap 12 of the auto-injector 10 described above is omitted and is replaced with an alternative cap 81.

The cap 81 of the auto-injector 80 of the seventh embodiment of the disclosure comprises a needle shield 82 and an outer cap 83. The outer cap 83 comprises inner and outer tubular portions 84, 85 which are concentrically aligned and extend from an end wall of the outer cap 83. The needle shield 82 is received within the inner tubular portion 84 of the outer cap 83 and is fixed thereto.

Figure 13:
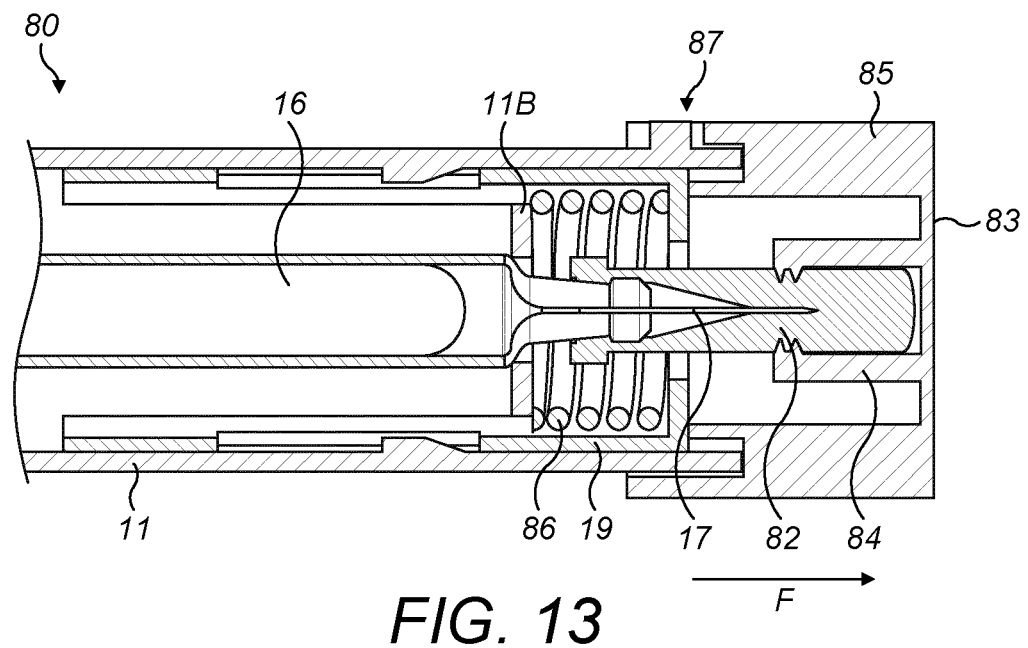
FIG. 13 is a schematic cross-sectional side view of the injection device of FIG. 12, wherein the cap is attached to the body.

The cap 81 is removably attachable to the body 11 such that a part of the outer tubular portion 85 of the outer cap 83 is received in the open distal end 11A of the body 11 to frictionally engage therewith. An end of the outer tubular portion 85 abuts the retractable sleeve 19 when the cap 81 is attached to the body 11 (as shown in FIG. 13). When the cap 81 is in this position, the needle shield 82 receives the needle 17 such that the needle 17 is shielded to prevent contamination of the needle 17 or injury to the patient.

Figure 14:
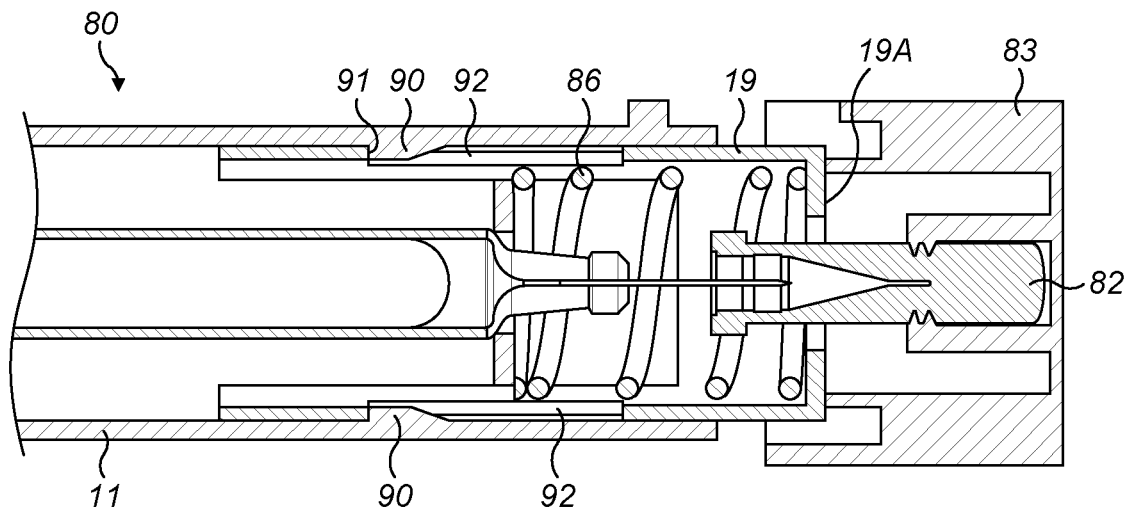
FIG. 14 is a schematic cross-sectional side view of the injection device of FIG. 12, wherein the cap is separated from the body.
Figure 15:
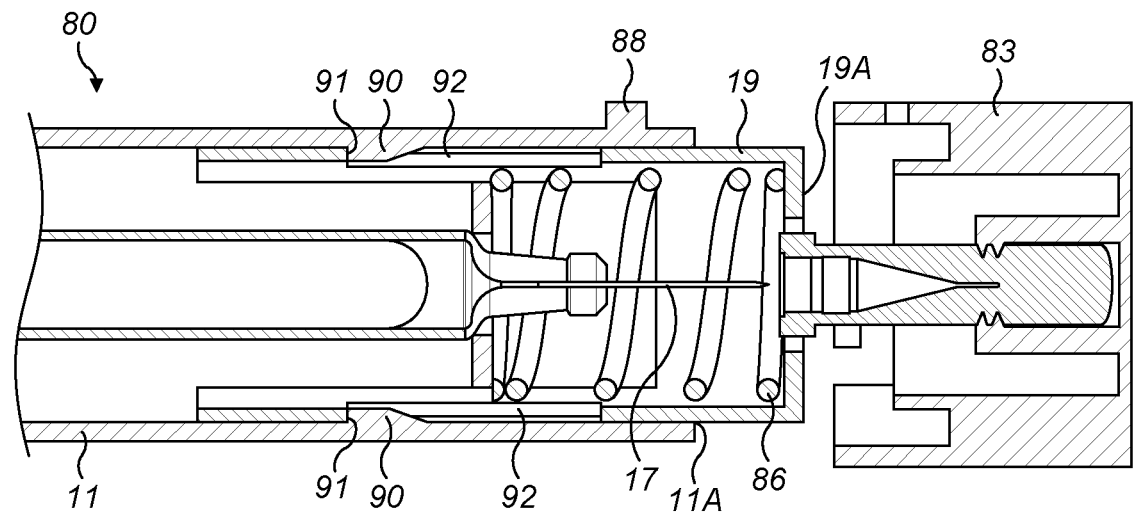
FIG. 15 is a schematic cross-sectional side view of the injection device of FIG. 12, wherein the cap is separated from the body and a retractable needle sleeve.
Figure 16:
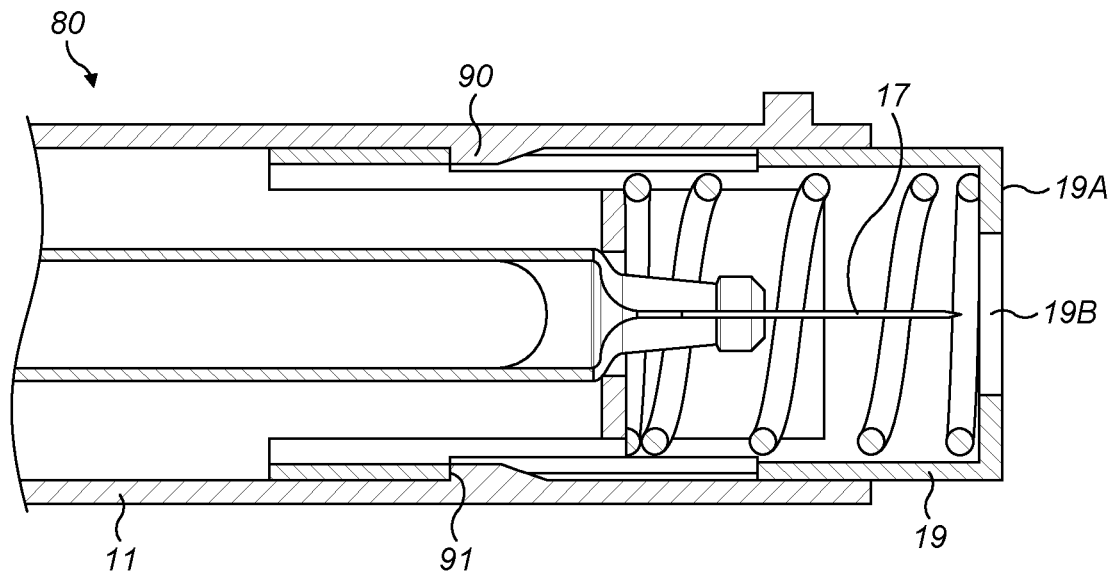
FIG. 16 is a schematic cross-sectional side view of the injection device of FIG. 12, wherein the cap is removed from the body and the retractable needle sleeve is in an extended position; and, FIG. 17 is a cross-sectional side view of the injection device of FIG. 12, wherein the cap is removed from the body and the retractable needle sleeve is in a retracted position.
Figure 17:
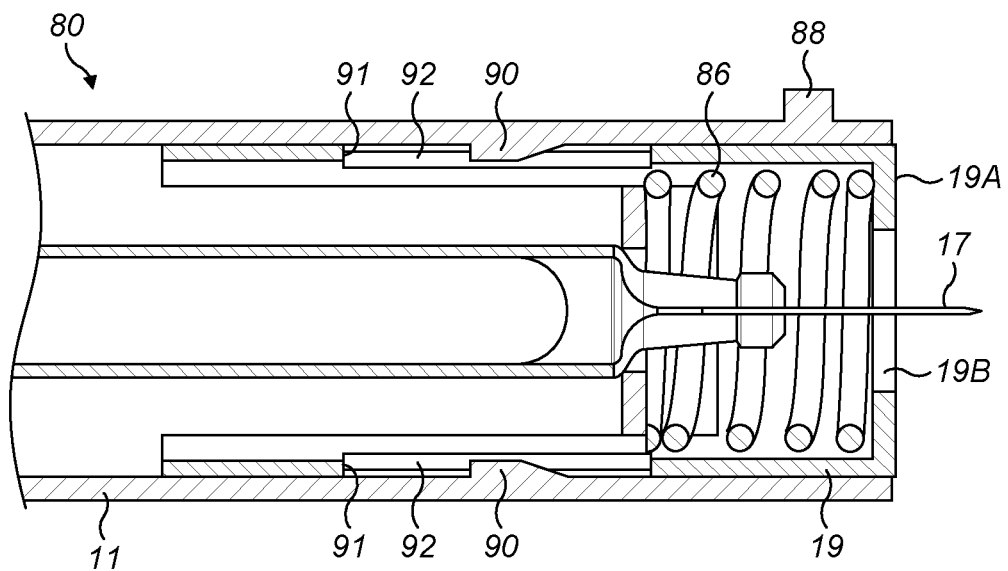

The retractable sleeve 19 is slidable relative to the body 11 between a retracted position (shown in FIGS. 13 and 17) and an extended position (shown in FIGS. 14 to 16). In the extended position, an end 19A of the retractable sleeve 19 extends axially past the needle 17 to shield the needle 17 to prevent the patient from being injured by the needle 17. When the retractable sleeve 19 is moved into the retracted position, the retractable sleeve 19 slides axially into the body 11 such that the needle 17 extends axially through an aperture 19B in the end 19A of the retractable sleeve 19 (as shown in FIG. 17).

The auto-injector 80 further comprises a biasing member 86 and a lock 87. The biasing member 86 is in the form of a helical spring 86. The spring 86 is located inside the retractable sleeve 19 such that the spring 86 extends about the central axis A-A of the auto-injector 80.

The body 11 comprises an internal shoulder 11B that extends radially from the peripheral wall of the body 11 towards the central axis A-A of the auto-injector 80. The spring 86 is compressed between the internal shoulder 11B of the body 11 and the end 19A of the retractable sleeve 19 when the retractable sleeve 19 is in the retracted position (as shown in FIGS. 13 and 17). Therefore, the spring 86 urges the end 19A of the retractable sleeve 19 axially away from the body 11 (in the direction of arrow 'F' shown in FIG. 13) such that the retractable sleeve 19 is biased into the extended position.

When the cap 81 is attached to the body 11 the end of the outer tubular portion 85 abuts the end 19A of the retractable sleeve 19 (as shown in FIG. 13) such that axial movement of the retractable sleeve 19 results in a force being exerted on the outer cap 83 by the end 19A of the retractable sleeve 19 to cause corresponding axial movement of the outer cap 83 and the needle sleeve 82. Therefore, the spring 86 also biases the cap 81 axially away from the body 11. Similarly, when the cap 81 is attached to the body 11 the outer tubular portion 85 abuts the end 19A of the retractable sleeve 19 to exert a force on the retractable sleeve 19 against the force of the spring 86 to cause the retractable sleeve 19 to be held in the retracted position.

The auto-injector 80 comprises first and second stops 90, 91 that are configured to limit the range of axial movement of the retractable sleeve 19 relative to the body 11. The body 11 comprises a pair of protrusions 90 that project radially inwardly from the peripheral wall of the body 11 to each form a first stop 90. The retractable sleeve 19 comprises a pair of slots 92 that are configured to slidably receive the pair of protrusions 90. The edge 91 of each slot 92 that is remote to the distal end D of the auto-injector 80 forms a corresponding second stop 91. Each first stop 90 abuts a corresponding second stop 91 when the retractable sleeve 19 is moved from the retracted position to the extended position to limit the amount that the retractable sleeve 19 can extend out of the body 11.

The lock comprises a plurality of latches 87. Each latch 87 comprises a pin 88 and a corresponding track 89. The pins 88 project radially outwardly from the peripheral wall of the body 11. The tracks 89 are L-shaped recesses in the outer tubular portion 85 of the outer cap 83. Each track 89 has a first track portion 89A and a second track portion 89B. The first track portions 89A extend axially from the end of the outer tubular portion 85 of the outer cap 83. Each second track portion 89B extends circumferentially from an end of a corresponding first track portion 89A.

Figure 12:
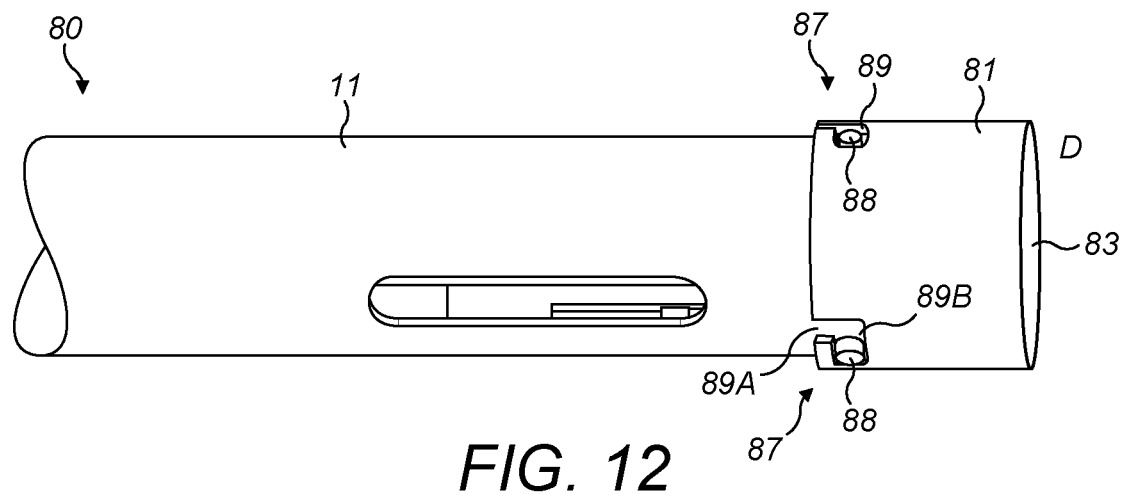
FIG. 12 is a schematic perspective view of part of an injection device according to a seventh embodiment of the disclosure, wherein a cap is attached to a body of the injection device.

The outer cap 83 is configured to be rotated relative to the body 11 about the central axis A-A of the auto-injector 80 to move the lock between a locked state and an unlocked state. When the lock is in the locked state, each pin 88 is received in the second track portion 89B of a corresponding track 89 (as shown in FIG. 12) to engage with the walls of the second track portion 89B such that axial movement of the outer cap 83 relative to the body 11 is prevented. To move the lock to the unlocked state, the outer cap 83 is twisted relative to the body 11 such that each pin 88 is moved circumferentially relative to the outer cap 83 into a corresponding first track portion 89A. When the lock is in the unlocked state, the pins 88 are free to move axially along the respective first track portions 89A towards the end of the outer cap 83 such that the outer cap 83 is able to move axially relative to the body 11. Therefore, the biasing force of the biasing member 86 is able to move the cap 81 axially away from the body 11 when the lock is moved from the locked state to the unlocked state.

The cap 81 is initially attached to the body 11 such that the needle 17 is completely received in the needle shield 82 and the lock is in the locked state (as shown in FIG. 13) to hold the cap 81 in position on the body 11 against the biasing force of the spring 86. Thus, the needle 17 is covered by the needle shield 82 to keep the needle 17 sterile and to prevent the needle 17 from causing injury to the patient. Furthermore, the end of the outer tubular portion 85 of the outer cap 83 abuts the end 19A of the retractable sleeve 19 such that the retractable sleeve 19 is held in the retracted position. Therefore, when the lock is in the locked state the cap 81 is held in place on the body 11 and the retractable sleeve 19 is held in the retracted position.

To inject medicament, the cap 81 is first removed from the body 11. Removal of the cap 81 from the body 11 is achieved by the patient exerting a force on outer cap 83 to twist the outer cap 83 relative to the body 11 about the central axis A-A of the auto-injector 80 such that the lock, and more specifically each latch 87 of the lock, moves from the locked state to the unlocked state.

This causes each pin 88 to move into a corresponding first track portion 89A such that the outer cap 83 is axially moveable relative to the body 11. Therefore, the lock no longer holds the retractable sleeve 19 and cap 81 in position relative to the body 11 against the biasing force of the spring 86 and so the biasing force of the spring 86 moves the end 19A of the retractable sleeve 19 away from the body 11 (in the direction of arrow 'F' in FIG. 13) such that the retractable sleeve 19 moves from the retracted position to the extended position (shown in FIG. 14). The end 19A of the retractable sleeve 19 is urged against the outer tubular portion 85 of the outer cap 83 such that the outer cap 83 is moved axially away from the body 11 as the retractable sleeve 19 moves to the extended position. The needle shield 82, which is fixed to the outer cap 83, is therefore also moved away from the body 11 until the cap 81 is separated from the body 11 and the needle 17 is partially removed from the needle shield 82 (as shown in FIG. 14).

With the outer cap 83 separated from the body 11 and the needle 17 partially removed from the needle sleeve 82 (as shown in FIG. 14), the outer cap 83 only loosely covers the end 19A of the retractable sleeve 19. Therefore, the patient is able to easily pull the outer cap 83 away from the retractable sleeve 19 (as shown in FIG. 15) until the cap 81 is completely separated from the retractable sleeve 19 so that the end 19A of the retractable sleeve 19 is exposed (as shown in FIG. 16).

With the cap 81 removed from the body 11 and retractable sleeve 19, the end 19A of the retractable sleeve 19 is pressed against an injection site of the patient such that the retractable sleeve 19 is slid into the body 11. Therefore, the retractable sleeve 19 is slid from the extended position (as shown in FIG. 16) to the retracted position (as shown in FIG. 17) so that the needle 17 extends through the aperture 19B in the retractable sleeve 19 and moves into the injection site of the patient to dispense medicament thereto. Thus, the biasing member 86 is configured to automatically move the retractable sleeve 19 into the extended position when the outer cap 83 is removed from the body 11 such that accidental injury to the patient is prevented. Furthermore, since the retractable sleeve 19 is biased into the extended position by the same biasing member 86 that is used to bias the cap 81 away from the body 11, the weight, cost and complexity of the auto-injector 80 is reduced in comparison to if a second biasing member was used for this purpose.

The spring 86 has a steep spring characteristic curve such that the spring 86 exerts a larger biasing force on the retractable sleeve 19 when the spring 86 is compressed than when it is partially extended. Therefore, a relatively large biasing force is exerted on the retractable sleeve 19 when the cap 81 is attached to the body 11 and the lock is in the locked state (as shown in FIG. 13). This helps to ensure that the biasing force of the spring 86 is sufficient to overcome frictional forces between the cap 81 and the body 11 and the needle 17 to move the cap 81 away from the body 11. Furthermore, the steep spring characteristic curve of the spring 86 results in a relatively small biasing force being exerted on the retractable sleeve 19 when the cap 81 is removed from the body 11 and the retractable sleeve 19 is in the extended position (as shown in FIG. 17) so that the force required to move the retractable sleeve 19 a small distance axially into the body 11 from the extended position to expose the needle 17 is relatively small. This reduces the force with which the end 19A of the retractable sleeve 19 must be pressed against the injection site of the patient in order to move the retractable sleeve 19 away from the extended position to expose the needle 17 during an injection, thereby improving the comfort of the patient.

Although in the above described embodiments the biasing member 26, 86 is in the form of a helical spring 26, 86, it shall be recognised that other types of biasing member are intended to fall within the scope of the disclosure. For example, the biasing member may alternatively comprise a different type of spring, such as a torsion spring, compression spring or clock spring. In another embodiment the biasing member comprises a resilient material that is compressed when the cap is attached to the body to act as a spring. In yet another embodiment, the biasing member comprises a pneumatic actuator. The pneumatic actuator may be configured to increase the air pressure in a chamber between the body and the cap or retractable sleeve in order to urge the cap axially away from the body. The pneumatic actuator may comprise a compressed air source that is fluidly coupled to the chamber. In yet another embodiment, the biasing member comprises a hydraulic actuator that is configured to urge the cap or retractable sleeve axially away from the body. The hydraulic actuator may comprise a hydraulically actuated piston that is arranged to urge the cap away from the body.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. An injection device comprising:
    a body for holding a syringe having a needle at one end thereof;
    a cap that is removably attached to the body and has an outer cap and a needle shield configured to frictionally engage with the syringe to cover the needle;
    a biasing member that is configured to urge the cap away from the body; and,
    a lock comprising a latch or bayonet connection that is moveable between a locked state, wherein the lock holds the cap and body together, and an unlocked state, wherein the cap and body are able to move apart,
    wherein the outer cap is rotatable relative to the body to move the lock to the unlocked state, and wherein a biasing force of the biasing member is configured to overcome friction between the cap and the body to separate the needle shield from the syringe in the unlocked state.

2. The injection device according to claim 1, wherein the biasing member is configured to bias the entire cap away from the body when the lock is in the unlocked state.

3. The injection device according to claim 1, wherein the biasing member is a helical spring.

4. The injection device according to claim 1, wherein the cap is moveable relative to the body in a first direction to move the lock from the locked state to an intermediate state, and wherein the cap is moveable relative to the body in a second direction distinct from the first direction to move the lock from the intermediate state to the unlocked state.

5. The injection device according to claim 1, wherein the lock comprises a track on one of the body and cap and a pin on the other one of the body and cap, wherein the track extends non-linearly and the pin is configured to be received in the track.

6. The injection device according to claim 5, comprising a projection in the track that is configured to resist movement of the pin in the track.

7. The injection device according to claim 1, further comprising a needle sleeve, wherein the needle sleeve is moveable relative to the body between an extended position, to shield the needle when a syringe is held within the body, and a retracted position, wherein the needle extends axially past an end of the needle sleeve, wherein the needle sleeve moves to the extended position when the lock is in the unlocked state and the cap is removed from the body.

8. The injection device according to claim 7, wherein the lock is configured such that when the cap is attached to the body the needle sleeve is urged into the body.

9. The injection device according to claim 1, comprising the syringe, wherein the syringe is received by the body, wherein the needle shield is in frictional engagement with the syringe when the cap is attached to the body.

10. The injection device according to claim 1, further comprising the syringe, wherein the syringe contains a medicament.

11. The injection device according to claim 1, wherein the injection device is an auto-injector.

12. The injection device according to claim 1, wherein the cap comprises the biasing member.

13. A method of removing a cap from an end of a body of an injection device, the cap comprising an outer cap and a needle shield to frictionally engage with a syringe, comprising the steps of:
  rotating the outer cap about a longitudinal axis of the body to move a lock of the injection device to a unlocked state, wherein the cap is held in place with the body against a force of a biasing member by the lock in a locked state prior to rotation of the outer cap, the lock comprising a latch or bayonet connection; and
  removing the cap from the end of the body, wherein the cap is urged away from the body by the force of the biasing member, and wherein the biasing force of the biasing member is configured to overcome friction between the cap and the body to separate the needle shield from the syringe in the unlocked state.

14. The method according to claim 13, wherein the biasing member is configured to bias the entire cap away from the body when the lock is in the unlocked state.

15. The method according to claim 13, wherein the biasing member is a helical spring.

16. The method according to claim 13, wherein the cap is moveable relative to the body in a first direction to move the lock from the locked state to an intermediate state, and wherein the cap is moveable relative to the body in a second direction distinct from the first direction to move the lock from the intermediate state to the unlocked state.

17. The method according to claim 13, wherein the lock comprises a track on one of the body and cap and a pin on the other one of the body and cap, wherein the track extends non-linearly and the pin is configured to be received in the track.

18. The method according to claim 17, wherein the injection device comprises a projection in the track that is configured to resist movement of the pin in the track.

19. The method according to claim 13, wherein the injection device comprises a needle sleeve, wherein the needle sleeve is moveable relative to the body between an extended position, to shield a needle when a syringe is held within the body, and a retracted position, wherein the needle extends axially past an end of the needle sleeve, wherein the needle sleeve moves to the extended position when the lock is in the unlocked state and the cap is removed from the body.

20. The method according to claim 19, wherein the lock is configured such that when the cap is attached to the body the needle sleeve is urged into the body.

* * * * *